United States Patent
Brandt

(10) Patent No.: US 7,904,314 B2
(45) Date of Patent: Mar. 8, 2011

(54) SYSTEM AND METHOD FOR ORDERING PATIENT SPECIFIC HEALTHCARE SERVICES

(75) Inventor: Samuel I. Brandt, Malvern, PA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 2169 days.

(21) Appl. No.: 10/142,470

(22) Filed: May 9, 2002

(65) Prior Publication Data

US 2003/0074220 A1    Apr. 17, 2003

Related U.S. Application Data

(60) Provisional application No. 60/329,991, filed on Oct. 17, 2001.

(51) Int. Cl.
*A61B 5/00* (2006.01)
*G06F 19/00* (2011.01)

(52) U.S. Cl. .......................... 705/3; 600/300
(58) Field of Classification Search ............... 705/2, 3; 600/300
See application file for complete search history.

(56) References Cited

U.S. PATENT DOCUMENTS

| | | | | |
|---|---|---|---|---|
| 6,018,713 A * | 1/2000 | Coli et al. | | 705/2 |
| 6,024,699 A * | 2/2000 | Surwit et al. | | 600/300 |
| 6,149,585 A * | 11/2000 | Gray | | 600/300 |
| 6,188,988 B1 | 2/2001 | Barry et al. | | 705/3 |
| 6,206,829 B1 | 3/2001 | Iliff | | 600/300 |
| 6,230,142 B1 | 5/2001 | Benigno et al. | | 705/3 |
| 6,234,964 B1 | 5/2001 | Iliff | | 600/300 |
| 6,283,761 B1 | 9/2001 | Joao | | 434/236 |
| 6,317,719 B1 | 11/2001 | Schrier et al. | | 705/2 |
| 7,076,436 B1 * | 7/2006 | Ross et al. | | 705/3 |

FOREIGN PATENT DOCUMENTS

JP    2000123098 A    4/2000

* cited by examiner

*Primary Examiner* — Luke Gilligan
(74) *Attorney, Agent, or Firm* — Alexander J Burke

(57) ABSTRACT

A system and method for ordering healthcare services wherein a list of selectable orders for medical services for a given patient is dynamically generated based on medical information of the patient (e.g., the patient's condition or set of conditions) and presented to a user (e.g., a physician). In one aspect, a system for ordering patient specific healthcare services comprises a user interface that enables a user to input a medical condition of a patient and to select desired medical services from a list of orderable medical services presented to the user; a services database comprising a plurality of predetermined medical services that are each associated with a medical condition; and an engine for compiling the list of orderable medical services from one or more predetermined medical services in the services database that are associated with the input medical conditions of the patient. A clinical knowledge model is used by the engine to identify a medical condition that is potentially associated with a known or identified medical condition of the patient, based upon potential etiology, potential complication, clinical associations, or any combination thereof.

20 Claims, 3 Drawing Sheets

Fig. 2

SYSTEM AND METHOD FOR ORDERING PATIENT SPECIFIC HEALTHCARE SERVICES

CROSS-REFERENCE TO RELATED APPLICATION

This application claims priority to U.S. Provisional Application No. 60/329,991, filed on 17 Oct. 2001.

TECHNICAL FIELD

The present invention relates generally to a system and method for ordering healthcare services and, in particular, a system and method for ordering healthcare services wherein a list of selectable orders for medical services for a patient is dynamically generated and presented to a user (e.g., physician) based on medical information pertaining to the patient.

DESCRIPTION OF RELATED ART

In general, a "physician order entry" application comprises a computerized system through which a physician can place an order for a medical service, etc, for a patient by selecting desirable items from a hospital's or health system's orderable services. Such orders may comprise, for example, one or more lab tests, medications, radiology procedures, or any other diagnostic test or therapeutic procedure.

Typically, physician order entry applications are designed with a view towards providing an easy and efficient method and user interface for finding and ordering such medical services. For example, some existing systems narrow down the list of selectable items and orderable services based upon the physician specialty (e.g., items that a surgeon would typically order). Other factors that are used for narrowing the list of orderable services include, for example, the hospital department (laboratory items), a personal favorite list (e.g., a physician's top 20 orders), or alphabetically listing medical services (e.g., all items starting with the letters "Amp"). Further, some conventional systems organize selectable medical services using "order sets", which comprise pre-built sets of orders that are typically created for a single specific clinical condition. These order sets may or may not be named after a patient condition (e.g., hip replacement order set). However, there are no known conventional systems that automatically present a set of orders in the context of more than one clinical condition, based upon the patient's known conditions.

While the above conventional systems support physician order entry for simple, uncomplicated patients, such systems are not efficient and straightforward for complex patients with more than one clinical problem. For those patients, the conventional systems force the physician to navigate through multiple options, piecing together the appropriate set of test and treatments for the patient, which can decrease efficiency and speed of placing orders. Moreover, conventional order entry systems can increase the risk that a physician overlooks diagnosis or treatment of a potential underlying or related condition for this complex patient.

Accordingly, a system and method that would provide an efficient and expedient protocol for ordering healthcare services for patients with complex and multiple clinical problems would be highly desirable.

SUMMARY OF THE INVENTION

The present invention is generally directed to a system and method for ordering healthcare services. Preferably, a list of selectable orders for medical services for a given patient is dynamically generated based upon medical information pertaining to the patient (e.g., the patient's condition or set of conditions.) The list of selectable orders is automatically generated and presented to a user (e.g., a physician) for selection of one or more orderable services by the user. The list of selectable orders is preferably generated by combining selectable items pertaining to each of multiple conditions into a single combined list of selectable items, that is specific to the patient. Since every patient is unique in having different combinations of clinical conditions, a system and method according to the present invention provides the sophistication to take into account any combination of clinical problems and translate these into a selection list of orderable services. Advantageously, the present invention shortens the list of selectable items, and organizes the selectable items into a clinical relevant hierarchy, thereby increasing speed and efficiency of ordering relevant medical services.

In another embodiment, a mechanism is provided to alert or otherwise remind the user (physicians) of particular items to order, in the context of the patient's medical information, that the user may have otherwise failed to consider, thereby reducing the risk of omission.

In one aspect of the present invention, a method for providing a displayable list of services available for order by a healthcare provider in providing health care to a patient comprises deriving search criteria based on a medical condition of a patient. The search criteria is applied in searching a database of predetermined services associated with a plurality of different medical conditions to identify candidate services for order by a user in providing health care addressing a medical condition of the particular patient. A list is then compiled of the identified candidate services. In one embodiment, the method is automatically performed in response to user command and without manual intervention.

In another aspect, a method for ordering healthcare services comprises inputting medical information of a patient and searching a database comprising predetermined medical services to identify one or more candidate medical services that are associated with the input medical information of the patient. A list of orderable medical services is compiled using the identified candidate medical services and the list of orderable medical services is presented to a user.

In yet another aspect of the present invention, a system for ordering patient specific healthcare services comprises a user interface that enables a user to input a medical condition of a patient and to select desired medical services from a list of orderable medical services presented to the user. The system further comprises a services database comprising a plurality of predetermined medical services that are each associated with a medical condition. An engine compiles the list of orderable medical services from one or more predetermined medical services in the services database that are associated with the input medical conditions of the patient.

In another aspect, the system comprises a clinical knowledge model that is used by the engine to identify a plurality of medical conditions that are potentially associated with a known or identified medical condition of the patient based upon potential etiology, potential complication, clinical associations, or any combination thereof.

In another aspect of the present invention, a user interface enables a user to input medical information of the patient directly from a patient database comprising medical information of one or more patients.

These and other objects, features and advantages of the present invention will be described or become apparent from the following detailed description of preferred embodiments, which is to be read in connection with the accompanying drawings.

BRIEF DESCRIPTION OF THE DRAWINGS

FIG. 2 is an exemplary diagram of a user interface for presenting a list of clinical services according to one aspect of the present invention.

DETAILED DESCRIPTION OF PREFERRED EMBODIMENTS

It is to be understood that the system and methods described herein in accordance with the present invention may be implemented in various forms of hardware, software, firmware, special purpose processors, or a combination thereof. Preferably, the present invention is implemented in software as an application (e.g., n-tier application) comprising program instructions that are tangibly embodied on one or more program storage devices (e.g., magnetic floppy disk, RAM, CD ROM, ROM, etc.), and executable by any device or machine comprising suitable architecture. It is to be further understood that since the constituent system modules and method steps depicted in the accompanying Figures are preferably implemented in software, the actual connections between the system components (or the flow of the process steps) may differ depending upon the manner in which the present invention is programmed. Given the teachings herein, one of ordinary skill in the related art will be able to contemplate these and similar implementations or configurations of the present invention.

Figure 1:
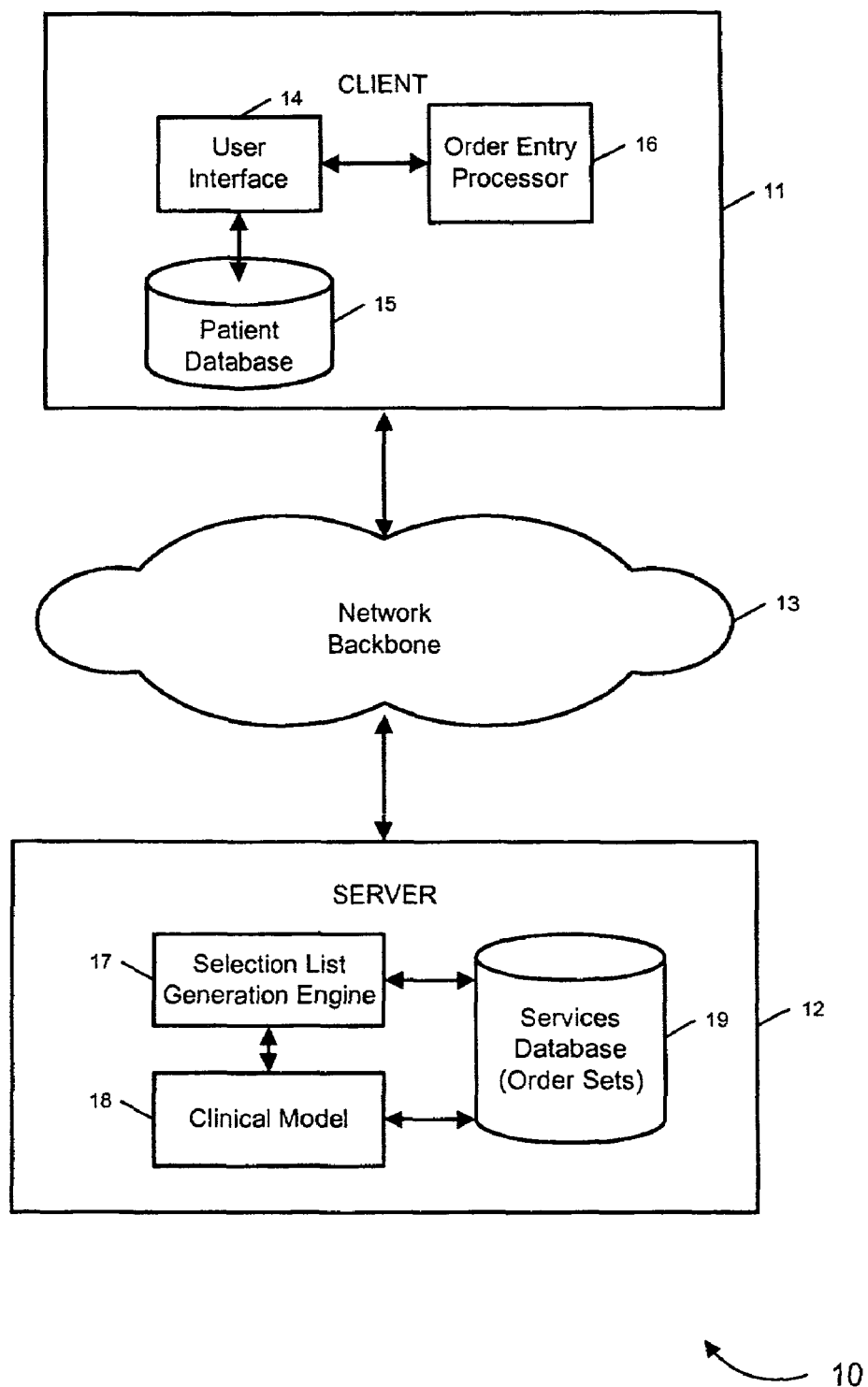
FIG. 1 is a block diagram of a system for ordering clinical services according to an embodiment of the present invention.

Referring to FIG. 1, a block diagram illustrates a system for ordering clinical services according to an embodiment of the present invention. A system 10 according to an embodiment of the invention comprises a client 11 comprising a physician order entry application for ordering clinical services (e.g., lab tests, medications, radiology procedures, diagnostic test or therapeutic procedures, etc.). A server 12, which is accessible by the client 11 over a network 13, comprises an application for generating a list of orderable clinical services for a given patient preferably based on patient medical information (such as clinical conditions and/or subcondition) provided by a user via the client 11.

It is to be understood that although a client-server framework is depicted FIG. 1, the system 10 may be implemented using any suitable computing environment framework such as P2P (peer-to-peer) or master/slave, for example. The network 13 may comprise any suitable network configuration such as an Intranet, a LAN (local area network), WAN (wide area network), P2P, a global computer network (e.g., Internet), a wireless communications network, or any combination thereof. Those of ordinary skill in the art can readily envision various architectures for implementing a system for ordering clinical services based on the teachings herein and nothing herein shall be construed as a limitation of the scope of the invention.

The client 11, which operates on, e.g., a user workstation, comprises a user interface module 14 for rendering, e.g., a GUI (graphical user interface) (or any other suitable interface such as a speech interface or combination speech/GUI interface) and an order entry engine 15 for generating application-specific entry forms/menus and interactive windows that are rendered by the user interface 14 and for processing orders selected by the user. A local database 15 comprises a repository of patient data of one or more patients. The patient data comprises medical information associated with one or more patients, which may be used by the user for ordering medical services. For example, when a user (e.g., physician) desires to obtain a list of orderable medical services for a given patient, the user will generate a list of one or more medical conditions of the patient via the appropriate user interface window. This query will then be sent to the server 12 for generating a list of orderable services based on the medical conditions of the patient.

The server 12 comprises business logic for serving client requests from the user workstation. The server 12 comprises an engine 17, a clinical knowledge model 18, and a database 19 of services. The engine 17 uses the model 18 to generate a list of orderable services (based on the medical conditions of the patient received in a client query) using data in database 19. The clinical model 18 comprises a model of a relationship between various clinical conditions and predetermined order sets stored in database 19. The predetermined order sets are preferably built on best practice choices. The clinical knowledge model 18 variably associates sub-conditions with one or more known or identified medical conditions of the patient based upon potential etiology, potential complication, or other clinical associations. The subconditions have the potential with varying degrees of probability to exist for the patient based upon their association with known medical conditions in the general clinical knowledge model.

The engine 17 compiles a list of orderable services for the patient by aggregating and organizing a plurality of order sets (in database 19) that are associated with, e.g., the known or identified medical conditions of the patient. As noted above, the clinical knowledge model 18 is used to associate subconditions with the known/identified medical conditions based upon potential etiology, potential complication, or other clinical associations. More specifically, a given patient has a collection of known medical conditions from a clinical perspective and each known medical condition has associated conditions based on, e.g., cause and effect. For example, chest pain (a known problem) may be caused by any number of conditions such as a heart attack, angina, a pulmonary embolism, or a pulled muscle. The conditions associated with chest pain can cause low oxygen saturation, risk of arrhythmia, etc. In accordance with the present invention, the system maps known/identified medical conditions of a patient to potential conditions associated with the known conditions based upon the clinical model 18. Preferably, the system 10 retrieves the relevant order sets associated with the patient's known/identified medical conditions, as well as those conditions that the patient may or may not have, but which are known to be clinically related to the patient's known conditions.

In the context of a given patient, the computer system has an understanding of the patient's clinical condition through a detailed problem list maintained by the physician. Any other data fields that indicate the patient's clinical condition are also factors that are considered when generating the list of orderable services. For example, if the patient is on Insulin, but for some reason "Diabetes" doesn't appear on the problem list generated by the physician, the system still can conclude that one of the patient's clinical conditions likely is Diabetes.

The system 10 provides the physician with a selection list from which to select orderable services, based on the patient's clinical conditions. The order sets are aggregated and organized so that the list of orderable services is useful and efficient. In one preferred embodiment, the selectable orders are listed based on a main condition, and the selection list may be further broken down based on subconditions, which allows a physician to evaluate each subcondition, and determine what services the physician would want to order to further diagnose or treat a particular subcondition.

Advantageously, by creating a specific selection list based on the patient's set of clinical conditions and subconditions, the system narrows down the domain of selectable items in a way that optimizes the selection process, but doesn't eliminate important items that apply to the patient.

In another embodiment, the system 10 adjusts the information presented to the clinician based on role and credentials of the clinician, and on the patient for which it is being delivered. For example, a surgeon would not typically treat patients with hypothyroidism. Therefore tests and treatments for hypothyroidism wouldn't typically appear on the surgeon's standard pick-list, or in the surgeon's order sets. The invention allows the patient's condition of hypothyroidism to present to the surgeon any tests (e.g. TSH), or therapies (e.g. levo-thyroxine) to the physician, which both facilitates the doctor's task of placing orders, but also eliminates the risk that the doctor overlooks to address the subcondition of hypothyroidism in the process of treating this patient.

Figure 2:
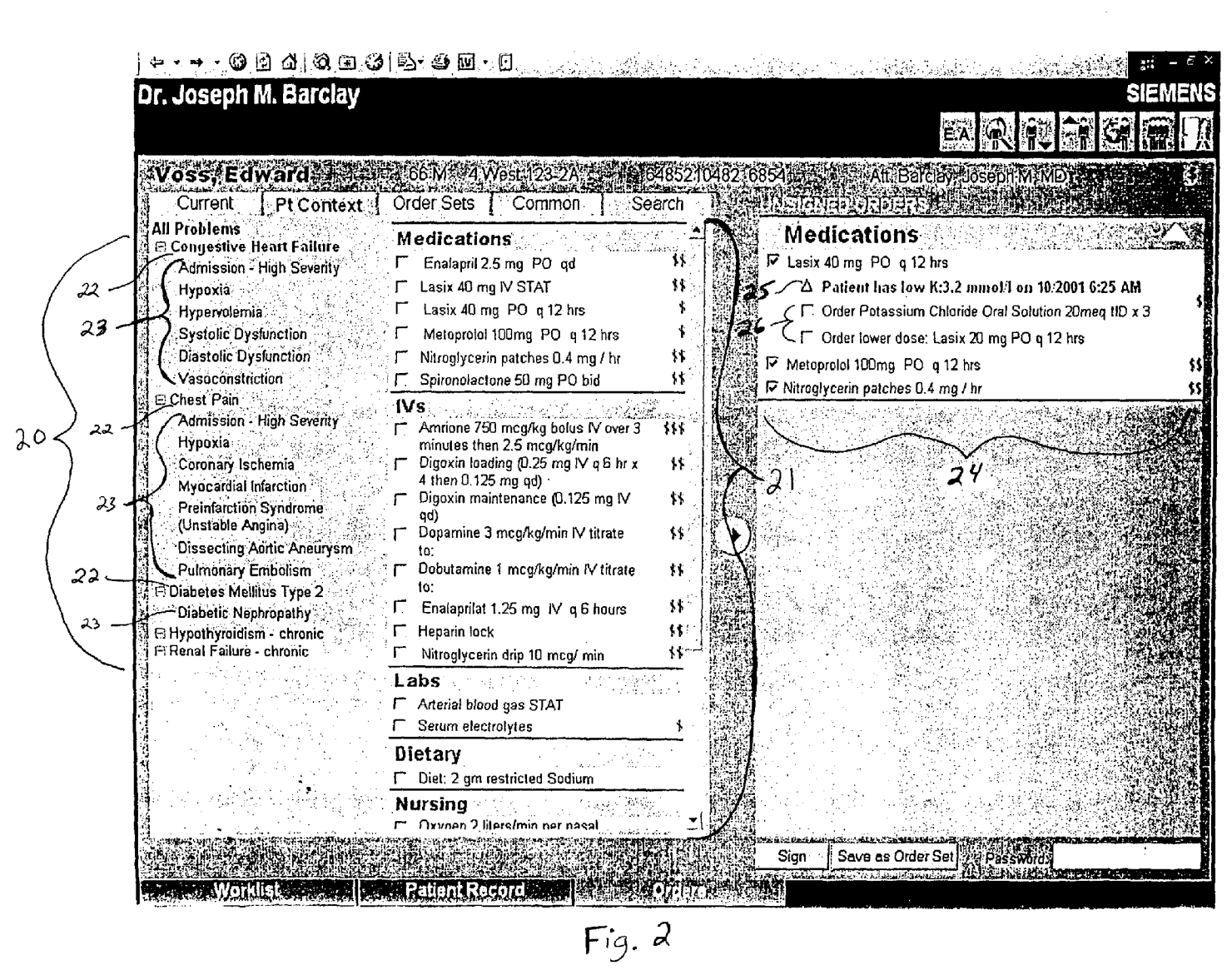

FIG. 2 is an exemplary diagram of a user interface for presenting a list of clinical services according to one aspect of the present invention. The exemplary user interface presents a list 20 of all medical conditions associated with a patient and a list 21 of selectable orders that is derived based on the patient's primary and underlying medical conditions. In particular, as noted above, the system utilizes a clinical knowledge model to identify conditions that are potentially associated with the patient's known/identified problems. In FIG. 2, a plurality of known/identified conditions 22 for the given patient are presented in the list 20 of conditions. Further, a set of possibly associated conditions 23 (which are identified by the clinical knowledge model) are presented for one or more of the patient's known/identified problems 22. For instance, as depicted in FIG. 2, for the known medical condition "chest pain" 22 of the patient, a plurality of potentially associated conditions 23, such as hypoxia and coronary ischemia, for example, are presented to the user. As explained above, these conditions are associated with individual order sets. The system then aggregates and organizes all of the orderable clinical services within these individual order sets into a single collection that is specific for each patient and presented in the list of selectable orders 21.

Furthermore, in the exemplary user interface of FIG. 2, as the user selects an order, the selected order is placed in an "unsigned orders" window 24 for review by the user prior to actual signing (ordering). The "unsigned orders" window 24 presents a list of selected orders for different medications, labs, nursing, etc. The user can review the selected orders in window 24 to confirm or exclude selected orders. In addition, orders can be presented in the context of alerts and reminders. For instance, when a special condition is identified (as indicated by reference numeral 25), a set of orders 26 that are relevant to the special condition 25 are displayed for selection by the clinician.

Advantageously, the present invention improves clinician efficiency because there is less information to search through, and quality of care is improved because only best practice care choices are made available to the ordering clinician.

Figure 3:
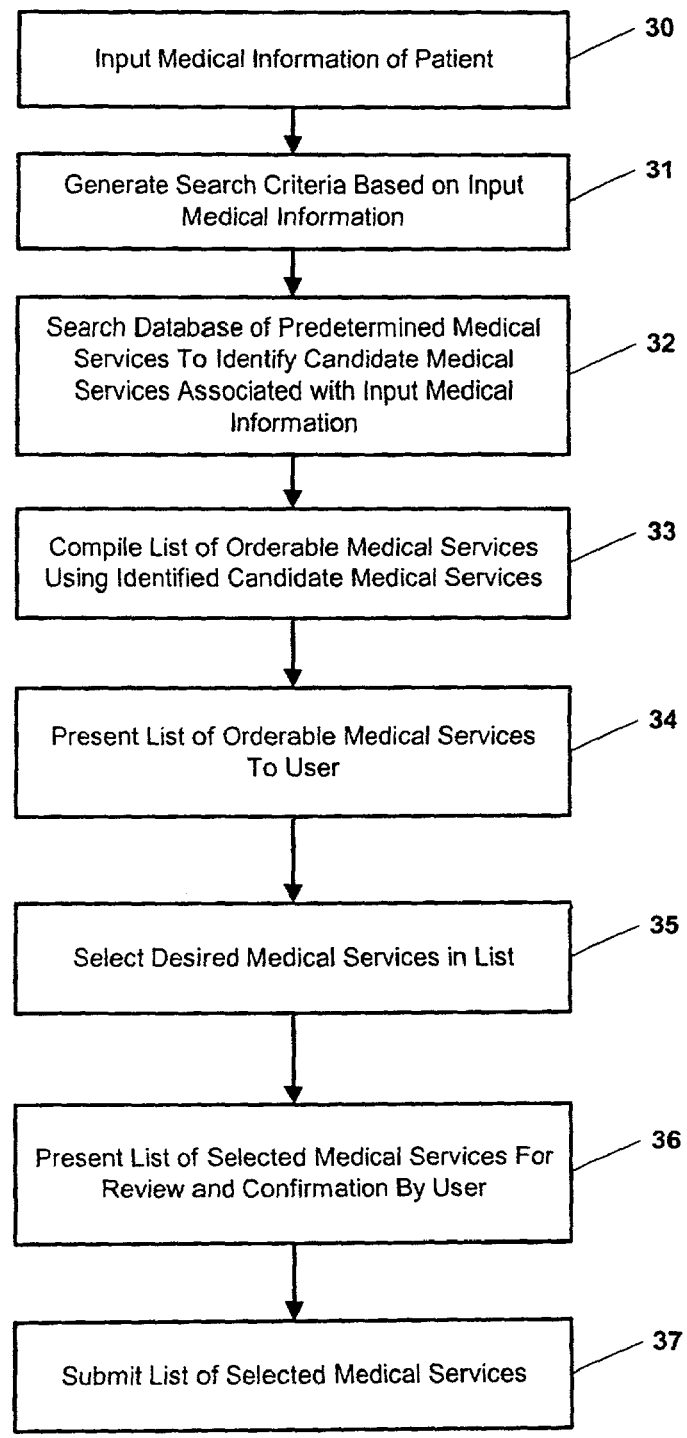
FIG. 3 is a flow diagram of a method for ordering clinical services according to an embodiment of the present invention.

Referring now to FIG. 3, a flow diagram illustrates a method for ordering clinical services according to an embodiment of the present invention. Initially, a user who wants to generate a list of orderable medical services for a patient will input medical information pertaining to the patient into the system via a user interface (step 30). The process of inputting medical information may be performed manually (e.g., by entering data into appropriate data fields in a GUI window, or via speech commands) or automatically (e.g., by having medical information of the patient automatically entered by selecting a patient file in a patient database).

The input medical information (and possible other information) is then used to generate search criteria for searching a database of predetermined medical services (step 31). For instance, in a preferred embodiment, the search criteria is based on one or more medical conditions of the patient, and/or one or more associated subconditions. Moreover, the search criteria may be further based on user preference information and/or based on the role of the user (e.g., physician, nurse, clinician, etc.).

Next, the derived search criteria is applied in searching the database of predetermined medical conditions to identify candidate medical services that are associated with the input medical information of the patient (step 32). It is to be understood that candidate medical services can be identified based on other information such as user preference information and/or the role of the user. Preferably, these candidate services comprise services that can be ordered by a user in providing health care addressing a medical condition of the particular patient.

Next, a list of orderable medical services is compiled using the identified candidate services (step 33). For example, the list may be compiled by aggregating and organizing a plurality of order sets that are associated with the identified medical conditions of the patient. To reduce redundancy, certain order sets that are common to one or more conditions are preferably listed once. In addition, the list of orderable services may be further narrowed based on user preference information, the role of the user, etc.

Once the list of orderable medical services is compiled, the list is presented to the user (step 34) via GUI interface, speech interface, etc, depending on the access device. For example, as described above, FIG. 2 is an exemplary diagram illustrating a GUI presentation of a list of orderable medical services. The user can select desired medical services from the list presented (step 35). Moreover, as indicated above, selectable orders can be presented in the context of alerts and reminders that are relevant to the special condition of the patient.

As the user selects desired medical service, a list of selected orders is generated and presented to the user for review and confirmation prior to actually ordering such services (step 36. When confirmed, the user can sign the order by activating the appropriate command to submit the list of selected medical services to the appropriate location (step 37).

Although illustrative embodiments have been described herein with reference to the accompanying drawings, it is to be understood that the present invention is not limited to those precise embodiments, and that various other changes and modifications may be affected therein by one skilled in the art without departing from the scope of the invention.

What is claimed is:

1. A method for providing a displayable list of services available for order by a healthcare provider in providing health care to a patient, comprising the steps of:
using a computer apparatus for,
automatically deriving search criteria indicating a known medical condition of a patient and a clinically related medical condition unidentified as a medical condition of said patient and determined by mapping of said known medical condition to a clinically related condition using stored information indicating conditions and problems of a patient;

automatically applying the search criteria in searching a database of predetermined services associated with a plurality of different medical conditions to identify candidate treatment services for order by a user in providing health care addressing a diagnosed medical condition and an associated medical sub-condition of the particular patient, said candidate treatment services for order being for treating said diagnosed medical condition and said associated medical sub-condition; and automatically compiling a list of the identified candidate treatment services.

2. The method of claim 1, wherein the step of automatically deriving search criteria comprises automatically deriving search criteria indicating a known medical condition and subconditions of a patient and a clinically related medical condition not indicated as being a known condition of said patient and identified by mapping of said known medical condition to a clinically related condition based on predetermined clinical information and displaying the compiled list of the identified candidate treatment services.

3. The method of claim 1, wherein
said candidate treatment services for order additionally including diagnostic services and address a medical condition and an associated medical sub-condition of the particular patient by treating said medical condition and said associated medical sub-condition,
the deriving step comprises deriving search criteria based on a plurality of medical conditions of the patient and
automatically adjusting a compiled list of the identified candidate treatment services in response to a role of a user.

4. The method of claim 3, wherein
the applying step comprises applying the search criteria in searching the database to identify a plurality of candidate treatment services associated with a corresponding plurality of known medical conditions of the patient for order by a user via a composite list of the plurality of candidate treatment services and
automatically adjusting a compiled list of the identified candidate treatment services in response to credentials of a user.

5. The method of claim 1, wherein
the deriving step comprises deriving search criteria indicating a plurality of medical conditions of the patient and potentially associated sub-conditions, wherein a potentially associated sub-condition of a medical condition is identified using a clinical knowledge model that associates medical conditions based upon one of potential etiology, potential complication, clinical associations, and a combination thereof.

6. The method of claim 1, wherein
the deriving step comprises deriving search criteria based on a role of the user.

7. The method of claim 6, wherein
the role of the user comprises a physician specialty or a nurse specialty.

8. The method of claim 1, wherein
the deriving step comprises deriving search criteria based on predetermined preferences of the user.

9. The method of claim 1, further comprising the step of receiving user identification information and wherein said steps of automatically deriving, automatically applying and automatically compiling are performed in response to a user command and without manual intervention.

10. The method of claim 9, comprising
the step of receiving information identifying a particular patient from a plurality of patients.

11. A program storage device readable by a machine, tangibly embodying a program of instructions executable by the machine to perform method steps for providing a displayable list of services available for order by a healthcare provider in providing health care to a patient, the method steps comprising:

automatically deriving search criteria indicating a known medical condition of a patient and a clinically related medical condition unidentified as a medical condition of said patient and determined by mapping of said known medical condition to a clinically related condition using stored information indicating conditions and problems of a patient;

automatically applying the search criteria in searching a database of predetermined services associated with a plurality of different medical conditions to identify candidate treatment services for order by a user in providing health care addressing a diagnosed medical condition and an associated medical sub-condition of the particular patient, said candidate treatment services for order being for treating said diagnosed medical condition and said associated medical sub-condition; and automatically compiling a list of the identified candidate treatment services.

12. The program storage device of claim 11, further comprising instructions for displaying the compiled list of the identified candidate treatment services and wherein the step of automatically deriving search criteria comprises automatically deriving search criteria based on a known medical condition and subconditions of a patient.

13. The program storage device of claim 11, wherein
the instructions for performing the step of deriving comprise instructions for deriving search criteria based on a plurality of medical conditions of the patient and
automatically adjusting a compiled list of the identified candidate treatment services in response to a role of a user.

14. The program storage device of claim 13, wherein
the instructions for performing the step of applying comprise instructions for applying the search criteria in searching the database to identify a plurality of candidate treatment services associated with a corresponding plurality of medical conditions of the patient for order by a user via a composite list of the plurality of candidate treatment services and
automatically adjusting a compiled list of the identified candidate treatment services in response to credentials of a user.

15. The program storage device of claim 11, wherein
the instructions for performing the step of deriving comprise instructions for deriving search criteria based on a plurality of medical conditions of the patient and potentially associated sub-conditions, wherein a potentially associated sub-condition of a medical condition is identified using a clinical knowledge model that associates medical conditions based upon one of potential etiology, potential complication, clinical associations, and a combination thereof.

16. The program storage device of claim 11, wherein
the instructions for performing the step of deriving comprise instructions for deriving search criteria based on a role of the user.

17. The program storage device of claim 16, wherein
the role of the user comprises a physician specialty or a nurse specialty.

18. The program storage device of claim 11, wherein
the instructions for performing the step of deriving comprise instructions for deriving search criteria based on predetermined preferences of the user.

19. The program storage device of claim 11, further comprising
instructions for performing the step of receiving user identification information and wherein the method is automatically performed in response to user command and without manual intervention.

20. The program storage device of claim 19, further comprising
instructions for performing the step of receiving information identifying a particular patient from a plurality of patients.

* * * * *